United States Patent [19]

Bréant

[11] 4,419,281

[45] Dec. 6, 1983

[54] N,N-DIETHYLHEPTANAMIDE FRAGRANCES

[75] Inventor: Claude Bréant, Villeurbanne, France

[73] Assignee: Rhone-Poulenc Industries, Paris, France

[21] Appl. No.: 302,672

[22] Filed: Sep. 15, 1981

[30] Foreign Application Priority Data

Sep. 26, 1980 [FR] France ............................... 80 20985

[51] Int. Cl.[3] ........................... A61K 7/46; C11B 9/00

[52] U.S. Cl. ........................... 252/522 R; 252/174.11; 424/65; 424/73

[58] Field of Search .......... 252/522 R, 522 A, 174.11; 424/65, 73

[56] References Cited

U.S. PATENT DOCUMENTS 4,228,044 10/1980 Camhre ............................... 252/547

OTHER PUBLICATIONS

Lutta et al., Chemical Abstracts, vol. 65, No. 12803h, (1966).

*Primary Examiner*—John F. Niebling

*Attorney, Agent, or Firm*—Burns, Doane, Swecker & Mathis

[57] ABSTRACT

Scents and perfumed compositions include, as an odorant therefor, an olfactory affecting amount of N,N-diethylheptanamide.

15 Claims, No Drawings

N,N-DIETHYLHEPTANAMIDE FRAGRANCES

CROSS-REFERENCE TO RELATED APPLICATIONS

My copending application, Ser. No. 136,545, filed Apr. 2, 1980, now U.S. Pat. No. 4,301,021 and Ser. No. 302,673, filed concurrently herewith, both assigned to the assignee hereof.

BACKGROUND OF THE INVENTION

1. Field of the Invention

The present invention relates to novel scents and perfume compositions, including novel perfume bases, and, more especially, to such scents and perfume compositions comprised of the odorant, N,N-diethylheptanamide.

2. Description of the Prior Art

The use of certain alkanoic acid amides for incorporating into perfume or insect repellent compositions has already been proposed to this art, but not one of such amides is either distinguished or characterized by any unique or original fragrance evoking a pleasant olfactory response. Thus, Einhorn et al, Ber., 39 1,223 (1906) report that N,N-diethyl-2-ethylbutanamide evolves a faint scent akin to that of menthol; French Pat. No. 1,572,332 notes that N,N-diethyldimethylpropanamide has a peppermint fragrance, while N,N-dimethyl-2-ethylbutanamide emits the fragrance of natural mint. In U.S. Pat. No. 3,909,452 there is attributed to N-phenyl-N-methyl-2-ethylbutanamide the odor of grapefruit, utilized in the formulation of food and herb aromas to develop a composition suitable for use as a base in perfumes having a lavender fragrance. Finally, A. S. Lutta et al, *Entomol. Obozrenie,* 45, 317-25 (1966) noted in a study of the insect repellent properties of the alkanamides, the agreeable odor of N,N-diethyloctamide, without reflecting upon any specific fragrance. It has since been determined that this particular amide has a weakly spicy odor that is relatively common. It too has been definitely ascertained that the amides of the $C_5$-$C_6$ alkanoic acids, with the exception of N-phenyl-N-methyl-2-ethylbutanamide, emit the more or less common mint odors. Furthermore, for a given acid, the character of the fragrance varies in direct response to the nature of the substituents borne by the amido nitrogen atom, but without, however, the ultimate fragrance evolved being at all predictable; thus, N,N-dimethyl-2-ethylbutanamide emits the fresh scent of natural mint, far stronger than that of the N,N-diethyl homolog, the scent of which latter derivative even though also being that of mint, being much weaker and more akin to that of peppermint. On the other hand, the molecular structure of the acid significantly affects the fragrance of the amide; thus, N,N-diethylcaprylamide evolves a scent considerably different from that of N,N-diethyl-2-ethylbutanamide. It logically follows, therefore, that it is difficult, if not impossible for those skilled in this art to reliably predict whether or not a given alkanamide will have a pleasing odor from an olfactory sensation point of view and, if so, just what that particular fragrance would be.

Indeed, perfumers have been determined that a pleasant smell for a pure product is not in and of itself sufficient reason to conclude that such product would be of value, e.g., in a perfume composition. In fact, for a fragrance to be useful in the perfume industry, it also must not adversely affect the other constituents of the composition, and must be compatible therewith. But compatibility cannot be predicted from scent, or fragrance alone.

Accordingly, the perfume industry is continuously seeking novel odorants and fragrances which by virtue of their uniqueness, availability and strength of scent are well adapted for formulation into perfume compositions which are completely unique.

SUMMARY OF THE INVENTION

Accordingly, a major object of the present invention is the provision of a novel odorant, and scents and perfume composition/formulations comprised thereof, all of which are characterized by an originally unique fragrance.

Briefly, the present invention features novel scents and perfume compositions/formulations, whether perfume bases or final perfume products, each of which is characterized in that, in addition to the typical perfume ingredients or components comprising same, if any, such products contain an effective fragrant, or fragrance attentuating amount of the odorant, N,N-diethylheptanamide.

DETAILED DESCRIPTION OF THE INVENTION

More particularly, the present invention features scents and perfume compositions/formulations, and perfume bases and perfumed products, each of which is characterized by including, as the active ingredient odorant thereof, an effective olfactory affecting amount of N,N-diethylheptanamide.

N,N-diethylheptanamide, which has the structural formula:

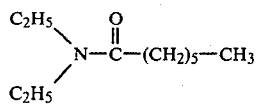

emits or gives off a fresh, penetrating spicy smell of jasmone, associated with the scent of rose leaves, which makes it especially valuable in compositions or fragrance bases imbued with the scent of jasmine, pepper or lavender, thus imparting more freshness and a more natural character to same.

By the expressions "perfume composition", "scent" or "formulation" any admixture of the different perfume ingredients, such as the typical solvents, solid or liquid perfume carriers, fixing agents, any one or more of the known fragrances or scents, and the like, and with which the N,N-diethylheptanamide is formulated or incorporated, such admixtures being utilized to impart to any type of substrate, or finished or final product, the particular fragrance desired. The perfume bases constitute preferred examples of the perfume compositions consistent herewith wherein the N,N-diethylheptanamide may be used to advantage. Other compositions wherein the subject compound may advantageously be incorporated are the conventional detergent compositions. These compositions typically comprise one or more of the following ingredients: anionic, cationic or amphoteric surface active agents, bleaching agents, optical bluing or whitening agents, fluorescent brighteners, various fillers and anti-redeposition ingredients. The nature of these different ingredients is not critical and the N,N-diethylheptanamide may be added to any type of detergent. Toilet waters, after-shave lotions, perfumes, soaps and deodorant and sanitary products, for example in aerosol form, are exemplary of those substrates and final products which can be uniquely scented with N,N-diethylheptanamide according to this invention.

N,N-diethylheptanamide is itself a colorless liquid, boiling at 105° C. under a pressure of 5 mm Hg, and is very soluble in the conventional organic solvents, such as the alcohols, ketones, esters or ethers.

The amount of N,N-diethylheptanamide in the various compositions according to the invention, expressed in percentage by weight in the particular composition under consideration, strictly depends on the nature of each such composition (perfume or toilet water base, for example) and the nature and intensity of the fragrance desired in the final product. It is thus obvious that in a perfume base the amount of N,N-diethylheptanamide may be very high, for example, higher than 50% by weight, and as much as 90% by weight, while in a perfume, a toilet water, an after-shave lotion or a soap, such amount may be considerably lower than 50% by weight. Thus, for all practical purposes the lower limit on the amount of N,N-diethylheptanamide is that amount which effects a perceptible modification in the odor, fragrance, or scent of the final product. In certain cases, this minimum amount may be on the order of 0.01% by weight. Obviously, amounts without the aforenoted range too may be utilized without departing from the scope of the present invention.

Morever, the N,N-diethylheptanamide incorporated per the invention is itself conveniently prepared by simply reacting a heptanoyl halide with diethylamine in the presence of an aqueous solution of an alkali metal base (preferably sodium or potassium).

In order to further illustrate the present invention and the advantages thereof, the following specific Examples are given, it being understood that same are intended only as illustrative and in nowise limitative.

EXAMPLE 1

300 g of N,N-diethylheptanamide were added to the following jasmine base:

| | | |
|---|---|---|
| (i) | Benzyl salicylate | 150 |
| (ii) | Benzyl acetate | 250 |
| (iii) | Linalol | 50 |
| (iv) | Orangeol | 25 |
| (v) | Indole | 2 |
| (vi) | Terpineol | 25 |
| (vii) | Alpha-amylcinnamaldehyde | 150 |
| (viii) | Linalyl acetate | 25 |
| (ix) | Ketone B | 1 |
| (x) | 3rd ylang-ylang oil | 22 |
| | | 700 g |

The composition obtained was compared with the base formulation.

N,N-Diethylheptanamide diminished the indole character of the base and imparts a fresh finely orange scent to the composition.

EXAMPLE 2

300 g of N,N-diethylheptanamide were added to the following peppery base:

| | | |
|---|---|---|
| (i) | Eugenol from vine tendrils | 150 |
| (ii) | Rhodiantal | 100 |
| (iii) | Pepper oil | 50 |
| (iv) | Clove oil | 100 |
| (v) | Phenylethyl alcohol | 100 |
| (vi) | Alpha-hexylcinnamaldehyde | 100 |
| (vii) | Cypress oil | 10 |
| | | 610 g |

-continued and the composition obtained was compared with the base.

N,N-Diethylheptanamide diminishes the chemical aspect of eugenol and imparts a fresh and natural spirit scent to the composition, together with a discreet scent having a spicy basic characteristic.

EXAMPLE 3

300 g of N,N-diethylheptanamide were added to the following lavender base:

| | | |
|---|---|---|
| (i) | Lavender oil | 250 |
| (ii) | Lavandin oil | 150 |
| (iii) | Aspic oil | 50 |
| (iv) | Coumarin | 25 |
| (v) | Ketone | 5 |
| (vi) | Linalyl acetate | 100 |
| (vii) | Terpenyl acetate | 120 |
| | | 700 g |

and the composition obtained was compared with the base.

N,N-Diethylheptanamide imparts strength, freshness and and amber-type harmonious scent to the composition.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. In a perfumed composition containing an admixture of perfume ingredients, the improvement which comprises, as an odorant therefor, an effective fragrance imparting amount of N,N-diethylheptanamide.

2. The perfumed composition as defined by claim 1, the same comprising at least one other fragrance in addition to said N,N-diethylheptanamide.

3. The perfumed composition as defined by claims 1 or 2, the same comprising a perfume solvent.

4. The perfumed composition as defined by claims 1 or 2, the same comprising a solid or liquid perfume carrier.

5. The perfumed composition as defined by claims 1 or 2, the same comprising a fixing agent.

6. The perfumed composition as defined by claim 1, comprising a detergent or soap.

7. The perfumed composition as defined by claim 1, comprising a toilet water.

8. The perfumed composition as defined by claim 1, comprising an after-shave lotion.

9. The perfumed composition as defined by claim 1, comprising a deodorant.

10. The perfumed composition as defined by claim 1, comprising a liquid perfume.

11. The perfumed composition as defined by claim 6, further comprising at least one member selected from the group consisting of a surfactant, a bleaching agent, an optical bluing or whitening agent, a fluorescent brightener, a filler and an anti-redeposition agent.

12. The perfumed composition as defined in claim 1, comprising from 50% to 90% by weight of N,N-diethylheptanamide.

13. The perfumed composition as defined by claim 1, comprising from 0.01% to 50% by weight of the N-N-diethylheptanamide.

14. The method of perfuming a substrate, comprising applying thereto the perfumed composition as defined by claim 1.

15. The method as defined by claim 14, said substrate being human skin.

* * * * *